United States Patent [19]

Lockhoff et al.

[11] Patent Number: 4,680,287
[45] Date of Patent: Jul. 14, 1987

[54] N-GLYCOSYLATED CARBOXAMIDE DERIVATIVES AS GROWTH-PROMOTERS IN LIVESTOCK FEEDING

[75] Inventors: Oswald Lockhoff, Cologne; Peter Stadler, Haan; Martin Scheer, Wuppertal; Friedrich Berschauer, Wuppertal; Anno de Jong, Wuppertal, all of Fed. Rep. of Germany

[73] Assignee: Bayer Aktiengesellschaft, Leverkusen, Fed. Rep. of Germany

[21] Appl. No.: 665,241

[22] Filed: Oct. 26, 1984

[30] Foreign Application Priority Data

Nov. 3, 1983 [DE] Fed. Rep. of Germany ....... 3339694

[51] Int. Cl.$^4$ ............................................. A61K 31/70
[52] U.S. Cl. ........................................ 514/42; 536/22; 536/53
[58] Field of Search .......................................... 514/42

[56] References Cited

FOREIGN PATENT DOCUMENTS

| 226474 | 3/1963 | Austria ................................. 514/42 |
| 0091645 | 10/1983 | European Pat. Off. ............. 424/180 |
| 0140321 | 5/1985 | European Pat. Off. ............. 514/42 |
| 0147777 | 7/1985 | European Pat. Off. ............. 514/42 |
| 1145418 | 3/1963 | Fed. Rep. of Germany ........ 514/42 |

OTHER PUBLICATIONS

Stedman's Medical Dictionary, 18th Rev. Ed., (1953), p. 1045.
A. L. Lehninger, "Digestion, Transport, and the Integration of Metabolism", Principles of Biochemistry, Chapter 24, pp. 683–691.
Dictionary of Immunology, Third Edition, pp. 170–173, (U. of Glasgow).
Roitt et al, "Immunology", Gower Med. Pub., (1985), pp. 1.1–1.6.
Buttery et al, "Control and Manipulation of Animal Growth", Butterworths, (1986), pp. 21–37.

Primary Examiner—Johnnie R. Brown
Attorney, Agent, or Firm—Sprung Horn Kramer & Woods

[57] ABSTRACT

Growth of animals is promoted by inclusion in their feed of compounds of the formula

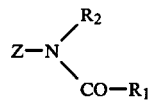

in which
Z is a glycosyl radical bonded via the anomeric carbon atom,
$R_1$ is hydrogen or an optionally substituted hydrocarbon radical having up to 30 Carbon atoms optionally interrupted by O, N or S, and
$R_2$ is hydrogen or an alkyl or aralkyl radical having up to 30 carbon atoms optionally interrupted by O or substituted by groups containing oxygen or by halogen, with the proviso that $COR_1$ is not an acyl group having 1–5 Carbon atoms when $R_2$ is an alkyl group having 10–20 carbon atoms.

6 Claims, No Drawings

N-GLYCOSYLATED CARBOXAMIDE DERIVATIVES AS GROWTH-PROMOTERS IN LIVESTOCK FEEDING

The invention relates to the use of compounds of the general formula I

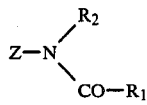

as growth-promoters in livestock feeding, and to livestock food, premixes and other agents which contain compounds of the formula I.

In formula I, $R_1$ denotes hydrogen or an optionally substituted, straight-chain or branched, saturated or singly or multiply unsaturated alkyl radical having from one to 30 carbon atoms, it being possible for this radical $R_1$ also to be interrupted by up to 5, preferably 1 or 2, O, S and/or N, with the proviso that —$COR_1$ does not represent an acyl group having 1–5 carbon atoms when $R_2$ denotes alkyl having 10–20 carbon atoms.

When the chain is interrupted by N, this nitrogen carries either H or a $C_1$-$C_{20}$—, preferably $C_1$-$C_5$—, alkyl radical or a —CO—alkyl radical, the latter alkyl group having 1–20, preferably 1–5, carbon atoms.

Preferred compounds of the formula I are those in which $R_1$ represents an alkyl or alkenyl radical having 1 to 21 carbon atoms, preferably 9 to 21 carbon atoms. Examples of saturated radicals which may be mentioned in this context are methyl, ethyl, propyl, i-propyl, butyl, i-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, docosyl, ethylpentyl, methyldecyl, i-propyldecyl or methyltridecosyl.

Examples of unsaturated radicals in the compounds used according to the invention are vinyl, 1-propenyl, 2-propenyl, i-butenyl, 1-butenyl, 2-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-decenyl, 5-decenyl, 9-decenyl, 8-heptadecenyl, 1,3-butadienyl, 1,3-pentadienyl, 1,4-pentadienyl, 2,4-pentadienyl, 8,11-heptadecadienyl and 8,11,14-heptadecatrienyl. In general, the unsaturated radicals having longer chain lengths are preferred, in particular singly or doubly unsaturated alkenyls having 7–21 carbon atoms.

In this context, the unsaturated hydrocarbon radicals can be in the form of pure cis or trans isomers or of mixtures of isomers.

Examples of compounds which are used according to the invention and in which the hydrocarbon radicals $R_1$ in formula I are interrupted by O, S and N or groups of corresponding atoms, or are substituted by groups containing these atoms or by halogen atoms are the methoxyethyl, hydroxyheptadecyl, oxobutyl, aminodecyl, N-methylaminodecyl, fluoromethyl, β-hydroxytridecyl or mercaptoethyl radical.

The hydrocarbon radicals $R_1$ in formula I can also contain phenyl radicals, it also being possible for these phenyl radicals optionally to be substituted by one to three substituents from the series comprising nitro and lower alkyl or by 1–5 halogen atoms.

$R_2$ in formula I represents hydrogen or a straight-chain or branched, saturated or singly or multiply unsaturated alkyl, cycloalkyl, alkylcycloalkyl or aralkyl radical having up to 30 carbon atoms, it also being possible for individual methylene or methine groups in the radical $R_2$ to be replaced by up to 5 oxygen or sulphur atoms or N, NH or N-lower alkyl groups. It is also possible for individual hydrogen atoms in the alkyl, cycloalkyl or aralkyl radicals to be substituted by up to 5 oxygen contained groups or halogen atoms.

Examples in which $R_2$ in formula I represents a straight-chain or branched, optionally singly or multiply unsaturated alkyl radicals are those mentioned for $R_1$.

The following may be particularly mentioned: ethyl, propyl, hexyl, decyl, dodecyl, tetradecyl, hexadecyl, octadecyl, docosyl, myricyl, ethylhexyl, isobutyl, propenyl, octenyl, hexadienyl, docosenyl, dimethylhexenyl and 2-(cyclohexyl)ethyl. The unsaturated hydrocarbons can be in the form of pure cis or trans isomers or of mixtures of isomers. Examples of hydrocarbon radicals $R_2$ substituted by groups containing oxygen atoms are hydroxypropyl and hydroxydimethyloctyl, examples of hydrocarbon radicals interrupted by oxygen atoms are alkoxyalkyl radicals, such as methoxybutyl or butoxypropyl, an example of a radical interrupted by N and O is 2-(N-morpholino)ethyl, and an example of a hydrocarbon radical substituted by halogen which may be mentioned is trifluoromethylethyl.

Exaples of aralkyl for $R_2$ in formula I are aryllower alkyl, such as benzyl, phenethyl or phenylhexyl, it being possible for the phenyl nucleus optionally to be substituted singly or multiply, preferably singly or doubly, for example by lower alkyl, trifluoromethyl, halogen, hydroxyl or lower alkoxy.

Lower alkyl or alkoxy are to be understood to be those radicals which contain 1–5, preferably 1–3, carbon atoms.

Z in the compounds of the formula 1 used according to the invention denotes a glycosyl radical which, in the compounds according to the invention, is always bonded to the amide nitrogen via the anomeric carbon atom, glycosyl radicals according to the invention being understood to be, in particular, monosaccharide, disaccharide and oligosaccharide radicals, in particular monosaccharides and disaccharides in which one or more hydroxyl groups can optionally be replaced by amino groups, acylamido groups, azido groups, hydrogen, nitro, thiol groups or lower alkoxy or halogen, and it also being possible for the glycosyl radicals to be in the form of the corresponding uloses, ulose derivatives, uronic acids or of uronic acid derivatives.

According to the invention, the glycosyl radicals Z in formula I are preferably in the pyranosyl or furanosyl form, the relevant monosaccharide, disaccharide or oligosaccharide radicals preferably being constructed of pentoses, hexoses and heptoses.

Examples of monosaccharide radicals in the compounds used according to the invention are glucopyranosyl, galactopyranosyl, mannopyranosyl, glucofuranosyl, ribofuranosyl, arabinopyranosyl or lyxopyranosyl or D-glycero-D-glucoheptopyranosyl radicals. Examples of disaccharide and oligosaccharide radicals which may be mentioned are maltosyl, maltotriosyl, maltotetraosyl, lactosyl, cellobiosyl, melibiosyl or 6-O-(α- or β-ribofuranosyl)-glucopyranosyl radicals, that is to say carbohydrate systems which are constructed of sugars having different C numbers, and in which the sugars can be in the pyranose and/or furanose form. The glycosidic bonds between the individual sugar units can be in the α- and/or β-form, and the glycosidic linkage of the individual sugar units can, starting from an anomeric carbon atom, take place both via the primary OH group and via one of the secondary hydroxyl groups of the saccharide moiety which is functioning as an aglycone.

Examples of monosaccharide, disaccharide and oligosaccharide radicals in which one or more OH groups are replaced by amino groups, acylamido groups, azido groups, hydrogen, nitro, thiol groups, lower alkoxy or halogen which may be mentioned for the compounds used according to the invention are 2-acetylamido-2-deoxyglucopyranosyl-, 2-amino-2-deoxyglucopyranosyl-, 4-azido-4-deoxyglucopyranosyl-, 4-stearoylamido-4-deoxy-D-glucopyranosyl-, 4-dodecoylamido-4-deoxy-D-glucopyranosyl-, 6-hexadecanoylamido-6-deoxy-D-galactopyranosyl-, 2,6-diamino-2,6-dideoxyglucopyranosyl-, 6,6'-diamino-6,6'-dideoxymaltosyl-, 6-amino-6,6'-dideoxylactosyl, 6-deoxymannopyranosyl-, 2-deoxyribofuranosyl-, fucosyl, 5-fluoro-5-deoxyribofuranosyl-, 6-O-methylglucopyranosyl, 6-deoxy-6-thioglucopyranosyl and 3-deoxy-3-nitrogalactopyranosyl.

When the glycosyl radicals are in the form of uronic acids or uronic acid derivatives, then they are glycuronic acids having a free carboxyl group or having a carboxyl group esterified by alkyl, or they are glycuronamide derivatives having an unsubstituted or substituted nitrogen atom. Examples of appropriate sugars are galacturonic acid, methyl glucuronate or N-dodecylglucuronamide.

The compounds of the formula I contain several chiral carbon atoms and are in the form of optically pure diastereomers or of mixtures of diastereomers. The compounds of the formula I used according to the invention are thus carboxamides or N-alkylated or N-aralkylated carboxamides which, in each case, carry a simple or modified monosaccharide, disaccharide or oligosaccharide radical having a N-glycosidic bond, that is to say via the anomeric carbon atom, to the amide nitrogen.

Very particularly preferred compounds used according to the invention are those demonstrated by exemplary embodiments, in particular those in Examples 12, 13, 14, 15, 16, 17, 18, 23, 24, 30, 31, 37, 42, 43, 44, 45, 46, 48, 49, 50, 53, 54, 55, 56, 57, 58, 59 and 60.

To prepare the compounds used according to the invention, first the sugars comprised by Z in formula 1 are reacted, either in the free, that is to say unprotected, form or in the form of protected and optionally activated derivatives, with an amino compound-$R_2$—$NH_2$, either in the free form or in the form of a suitable acid addition salt, with the meaning for $R_2$ described above, and then the glycosylamaine thus obtained is acylated using a carboxylic acid derivative, which is, as customary for acylation reactions, activated and, where appropriate, has functional groups protected and the protective groups which are, where appropriate, present in the reaction product thus obtained are split off, and in this manner the compounds of the formula I are obtained and, if necessary, they can be purified by chromatography, recrystallization, extraction or the like.

In a preferred embodiment, in a manner known per se, in a first process step, the unblocked sugar Z—OH, OH representing the anomeric hydroxyl group and Z having the meaning described in formula I, is reacted in a suitable solvent, or without solvent, where appropriate in the presence of a catalyst, at temperatures between 0° C. and 80° C., with 1 to 10 equivalents of the relevant amine $R_2$—$NH_2$, and the relevant glycosylamines Z—NH—$R_2$ are obtained after working up, usually in high yields, as amorphous or crystalline solids or as viscous syrups.

In the second process step, the glycosylamine Z—NH—$R_2$ is reacted with 1-10 equivalents of a carboxamide derivative of the formula $R_1$—CO—X, in which $R_1$ has the abovementioned meaning and X designates halogen or a leaving group customarily used in acylation reactions, preferably an activated ester radical, or a group O—OC—$R_1$ having the abovementioned meaning for $R_1$, the reaction being carried out in an organic or aqueous-organic solvent at temperatures between 0° C. and 50° C., optionally in the presence of a base, and, when reaction is complete, the reaction product is worked up in a customary manner.

In the case where one or more free amino groups are present in the carbohydrate radical Z, these are provided with an amino protective group in a manner known per se before the reaction with the amine $R_2$—$NH_2$.

Suitable amino protective groups are those groups customarily used in sugar and peptide chemistry (see, for example, HOUBEN-WEYL, Methoden der organischen Chemie (Methods of Organic Chemistry), Volume XV, published by Georg Thieme, Stuttgart, 1974), which, on the one hand, are stable under the reaction conditions applying but, on the other hand, can be split off again after the preparation of the relevant N-glycoside and its subsequent acylation with a carboxylic acid derivative $R_1$—CO—X, with the abovementioned meaning for $R_1$, so selectively that the desired final product of the formula I is obtained, that is to say without the acylamino group contained in the final product of the formula I being after cleaved. Preferred examples are acyl groups of the type

where B denotes trichloromethyl or trifluoromethyl, or of the type

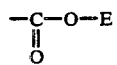

where E represents, for example, trichloroethyl or tertiary butyl, or sulphenyl groups of the type

where G represents phenyl, substituted phenyl or diphenylmethyl or triphenylmethyl, and 'substituted phenyl' designates a phenyl radical which is substituted by one to three substituents from the series comprising nitro and lower alkyl or by 1 to 5 halogen atoms, preferably chlorine atoms. Examples which may be mentioned are the 2,4,5-trichlorophenylsulphenyl and the o-anitrophenylsulphenyl radical.

The introduction of these protective groups into the amino compounds and their subsequent splitting off to liberate the desired amino groups are known and are described, for example, in the literature reference cited above.

In another embodiment of the process for the preparation of those products of the formula I in which one or more free amino groups are present in the glycosyl radical Z, sugar derivatives Z—OH are used as starting materials, in which the amino group or the amino groups are initially in the form of azido radicals, that is to say in a masked form. In the concluding step of the preparation of the compounds of the formula I, these azido groups are converted by reduction, in a manner known per se, into amino groups, care being taken that the reducing agents used are such as do not attack the other groups which are, where appropriate, present in the molecule and are sensitive to reduction.

Appropriate azido sugars and their preparation are known (see, for example, Methods in Carbohydrate Chemistry, Vol. I, 242–246, Academic Press, 1962, New York and London). It is possible to use for the reduction hydride donors, such as, for example, sodium boranate or lithium alanate, catalytically activated hydrogen or triphenylphosphine in methanol/ammonia/pyridine or hydrogen sulphide or mercaptans in protic solvents.

It is possible to use as the solvent all conventional organic solvents, preferably lower alkanols, but also water or aqueous alkanols.

The reactions are carried out, where appropriate, with the addition of organic acids, such as acetic acid, or inorganic acids, such as sulphuric acid, or with the addition of organic bases, such as, for example, pyridine, or inorganic bases, such as, for example, ammonia. It is carried out at temperatures between 0° and 120° C., preferably 10° C. to 40° C., where appropriate under elevated pressure and/or intergas.

In the case where one or more OH groups in the carbohydrate moiety Z in the compounds of the formula I are replaced by one or more acylamido groups, the sugars Z—OH are used from the outset in the form of the corresponding acylamido sugars. The acylamido sugars are then first reacted at the anomeric center with the above-mentioned amines to give the corresponding acylamidoglycosylamines and, in the second reaction step, are acylated on the C-1 amino group of the sugar moiety to give N-(acylamidoglycosyl)amides of the formula I.

Another procedure for the preparation of compounds of the formula I in which Z represents a sugar radical substituted by one or more acylamido groups comprises reacting aminodeoxysugars which carry the amino group on a carbon atom other than the anomeric carbon atom with amines of the formula $R_2$—$NH_2$ to give (aminodeoxyglycosyl)amines which then, in a second reaction step, undergo double or, where appropriate, multiple acylation to give N-(acylamidoglycosyl)amides of the formula I

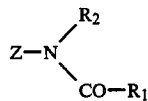

Furthermore, it is also possible to obtain the compounds of the formula I in which Z represents a sugar radical which is substituted by one or more acylamido groups by preparing derivatives of the formula I in which Z initially represents an amino sugar protected by one or more temporary amino protective groups of the type described above,

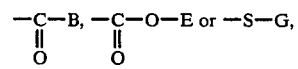

splitting off the temporary amino protective groups by the customary methods to give the corresponding N-(aminodeoxyglycosyl)amides and then reacting the latter with activated carboxylic acid derivatives to give the corresponding N-(acylamidoglycosyl)amides of the formula I

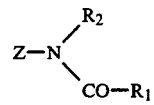

Another procedure for the preparation of N-(acylamidoglycosyl)amides of the formula I comprises reacting, by the customary methods, N-(azidoglycosyl)amides of the formula I to give the N-(aminoglycosyl)amides of the formula I and then acylating the latter with activated carboxylic acid derivatives to give N-(acylamidoglycosyl)amides of the formula I.

The first process step for the preparation of the compounds of the formula I is thus the reaction of a sugar Z—OH, with an amine of the type $R_2$—$NH_2$ at the anomeric carbon atom, with water being split off, to give the relevant glycosylamine.

Amines $R_2$—$NH_2$ which are liquid at room temperature can be reacted with the sugar directly, that is to say without solvent. This reaction is carried out at temperatures between 0° C. and 100° C., preferably at 25° C. to 70° C. Suitable catalysts are mineral acids, such as, for example, hydrochloric acid, sulphuric acid or nitric acid, or short-chain carboxylic acids, such as acetic acid or propionic acid, which are used in amounts of from 0.001 to 0.05 equivalents.

It is possible in every case, and it is also preferred for amines $R_2$—$NH_2$ which are solid at room temperature, to carry out the preparation of the glycosylamines in the presence of a solvent. This reaction is then preferably carried out in the presence of a diluent which is inert under the reaction conditions and whose nature is preferably such that, at the least, either the reactants or the reaction product dissolve in it.

Alcohols, such as methanol, ethanol, 1-propanol and 2-propanol, ethers, such as tetrahydrofuran and dioxane, and dimethylformamide are suitable, the addition of water being preferred except when the alcohols are used. Furthermore, water alone is also suitable as the solvent, and is preferable for short-chain amines $R_2$—$NH_2$. It can also be an advantage to use the alkanols mixed with water.

When solvents are used for the preparation of the glycosylamine, the reaction temperatures are between −10° C. and 120° C., preferably between 30° C. and 70° C.

The relevant diluent can be added before or during the reaction, as chosen. Addition before the reaction is preferred for long-chain amines $R_2$—$NH_2$.

The glycosylamines prepared as described above crystallize out either immediately or after cooling, or can be precipitated or induced to crystallize by the addition of suitable less polar auxiliary solvents, such as acetone, diethyl ether, cyclohexane, ethyl acetate or petroleum ether, where appropriate with cooling, and, where appropriate, excess amine $R_2$—$NH_2$ which is present can be removed by washing or recrystallization of the product in a manner known per se.

The second process step for the preparation of the compounds of the formula I is the selective N-acylation of a glycolsylamine, which has been obtained as described above, using a carboxylic acid derivative of the formula $R_1$—CO—X, with the abovementioned meaning of $R_1$ and X. Carboxylic acid derivatives R—CO—X which are known per se and are to be preferred are anhydrides, activated esters and acid halides, preferably chlorides.

These acylating agents are preferably reacted with the glycosylamines in the presence of a diluent in which the reactants are completely or only partially dissolved.

Organic or inorganic solvents are suitable, preferably those which, under the reaction conditions, suppress or prevent side reactions where possible. The reaction can be carried out both in organic solvents, such as ethers, for example tetrahydrofuran and dioxane, or alcohols, for example ethanol and propanol, or ketones, for example acetone or methyl ethyl ketone, or in dimethylformamide, ethyl acetate or pyridine, and in mixtures of these solvents with one another and/or with water. The use of anhydrous solvents is generally to be preferred.

The acylating agents $R_1$—CO—X are used in 1-10 equivalents relative to glycosylamine, the use of 1-3 equivalents being preferred.

It is possible, preferably when using acid halides and anhydrides, to carry out the acylation reactions in the presence of basic auxiliaries. All basic compounds customary in organic synthesis can be used, such as, for example, tertiary aliphatic or aromatic amines, or alkali metal and alkaline earth metal hydroxides and carbonates, such as sodium hydroxide solution, sodium carbonate or calcium carbonate.

The acylations are carried out at temperatures between about $-30°$ C. and $+80°$ C., preferably between $-10°$ C. and $+20°$ C.

The amides obtained in this manner are isolated by processes known per se in the form of crystalline or amorphous solids or as viscous syrups and, where necessary, purified by recrystallization, chromatography, extraction etc.

In the case of compounds having protected amino groups in the glycosyl moiety, the protective groups are split off in a manner known per se.

The diagram below is intended to illustrate one of the preferred embodiments of the preparation of compounds of the formula I by means of an example:

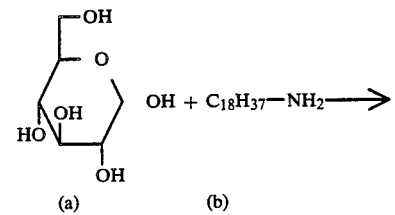

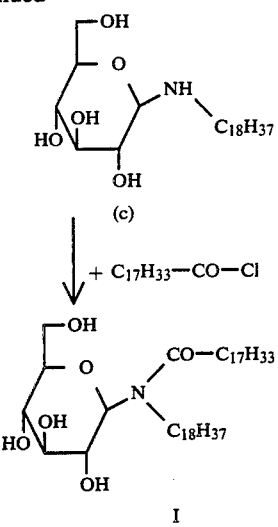

In the first process step, glucose (a) is reacted with octadecylamine (b) to give N-octadecyl-$\beta$-D-glucopyranosylamine (c) which, in the second process step, is acylated with oleoyl chloride to give N-octadecyl-N-oleyl-$\beta$-D-glucopyranosylamide (I).

It is also possible according to the invention to use salts of the compounds of the formula I. These are primarily the customary physiologically acceptable, non-toxic salts, for example alkali metal or ammonium salts.

Surprisingly, the glycosylamides of the formula (I) have the property of promoting and accelerating the growth of livestock, so that these compounds can be used for the purposes mentioned in all areas of livestock breeding and livestock management.

In this context, the efficacy of the compounds used according to the invention is essentially independent of the species and sex of the livestock. The compounds of the formula (I), according to the invention, prove to be particularly valuable for the rearing and maintenance of young and fattening livestock. Examples of livestock for which the compound can be used to promote and accelerate growth and which may be mentioned are the following useful and ornamental species:

Warm-blooded animals, such as cattle, pigs, horses, sheep, goats, cats, dogs, rabbits, fur-bearing animals, for example, mink and chinchilla, poultry, for example chickens, geese, ducks, turkeys and broilers, pigeons, parrots and canaries, and cold-blooded species, such as fish, for example carp, and reptiles, for example snakes.

Glycosylamides of the formula (I) are preferably used for the rearing and maintenance of ruminants, such as calves, goats and sheep, and for pigs and chickens.

The amount of glycosylamides of the formula (I) which is administered to the livestock to achieve the desired effect can be varied within wide limits. It is preferably about 0.1 to 500, in particular 0.1 to 100, mg kg of body weight per day. The duration of administration can range from a few hours or days up to several years. The appropriate amount of active compound and the appropriate duration of administration depend on, in particular, the species, the age, the sex, the state of health and the type of management of the livestock, and they can be readily determined by all those skilled in the art.

The compounds are administered to the livestock by the customary methods. The mode of administration depends on, in particular, the species, the behavior the state of health of the livestock. Thus, administration can be carried out orally or parenterally, once or several times a day, at regular or at irregular intervals. In most cases, for reasons of convenience, oral administration is to be preferred, in particular during the cycle of intake of food and/or drink by the livestock.

The compounds can be administered as the pure substances or in the form of formulations, that is to say mixed with non-toxic, inert vehicles, and as such is to be understood every type of solid, semi-solid or liquid diluent, filler and formulating auxiliary.

It is possible for glycosylamides of the formula (I), where appropriate in the form of a formulation, also to be administered together with pharmaceutically active compounds, mineral salts, trace elements, vitamins, proteins, lipids, colorants and/or flavorings in a suitable form.

Oral administration together with the feed and/or drinking water is to be recommended, the active compounds being added, depending on requirements, to the total amount or to only portions of the feed and/or drinking water.

The compounds can be added to the feed and/or drinking water by customary methods, by simply mixing as the pure substances, preferably in finely divided form, or in the form of a formulation mixed with edible non-toxic vehicles, and, where appropriate, in the form of a premix or a feed concentrate.

For example, the feed and/or drinking water can contain the active compound according to the invention at a concentration of about 0.1 to 100, in particular 0.5 to 10.0, ppm. The optimal concentration level of the active compound in the feed and/or drinking water depends, in particular, on the amount of feed and/or drinking water consumed by the livestock, and this can readily be determined by all those skilled in the art.

The type of the feed and its composition is irrelevant in this context. It is possible to use all customary, commercial or special compounded feeds which preferably contain the usual balance of energy carriers and builders, including vitamins and minerals, for a balanced diet. The feed can be composed of, for example, plant materials, for example hay, beet, cereals, cereal by-products, animal materials, for example, meat, lipids, bonemeal, fish products, vitamins, for example vitamin A, D complex and B complex, proteins, aminoacids, for example DL-methionine, and inorganic materials, for example lime and sodium chloride.

Feed concentrates contain glycosylamides of the formula (I) in addition to edible materials, for example ryemeal, corn meal, soy bean meal or lime, where appropriate with other nutrients and builders and with proteins, mineral salts and vitamins. They can be prepared by the customary mixing methods.

It is possible, preferably in premixes and feed concentrations, for the active compounds, where appropriate, also to be protected from air, light and/or moisture by suitable agents covering its surface, for example with non-toxic waxes or gelatine.

An example for the composition of a chicken rearing feed which contains glycosylamides of the formula (I):

200 g of wheat, 340 g of corn 361 g of soy meal, 60 g of beef tallow, 15 g of dicalcium phosphate, 10 g of calcium carbonate, 4 g of iodized sodium chloride, 7.5 g of vitamin/mineral mixture and 2.5 g of active compound premix provide, after thorough mixing, 1 kg of feed.

The vitamin/mineral mixture comprises the following:

6,000 I.U. of vitamin A, 1,000 I.U. of vitamin $D_3$, 10 mg of vitamin E, 1 mg of vitamin $K_3$, 3 mg of riboflavin, 2 mg of pyridoxine, 20 mg of vitamin $B_{12}$, 5 mg of calcium pantothenate, 30 mg of nicotinic acid, 200 mg of choline chloride, 200 mg of Mn $SO_4 \times H_2O$, 140 mg of Zn $SO_4 \times 7$ $H_2O$, 100 mg of Fe $SO_4 \times 7$ $H_2O$ and 20 mg of Cu $SO_4 \times 5$ $H_2O$.

The active compound premix contains glycosylamides of the formula (I) in the desired amount, for example 100 mg, and also contains 1 g of DL-methionine and sufficient soy bean meal to produce 2.5 g of premix.

An example for the composition of a pig rearing feed which contains the active compound according to the invention:

630 g of cereal meal feed (composed of 200 g of maize, 150 g of barley meal, 150 g of oatmeal and 130 g of wheat meal), 80 g of fishmeal, 60 g of soy meal, 60 g of cassava meal, 38 g of egg yeast, 50 g of vitamin/mineral mixture for pigs (composition, for example, as for chicken feed), 30 g of linseed cake meal, 30 g of corn gluten feed, 10 g of soy oil, 10 g of sugarcane molasses and 2 g of active compound premix (composition, for example, as for chicken feed) provide, after careful mixing, 1 kg of feed.

The abovementioned mixed feeds are preferably intended for rearing and fattening chickens and pigs respectively, but they can also be used with the same or similar composition for rearing and fattening other livestock.

14-day feeding trials on chickens and 6-week feeding trials on broilers which contained 0.1 ppm to 2.0 ppm of compound of the formula (I) with the feed showed pronounced gains in weight by the livestock treated with the glycosylamides of the formula (I) compared with the livestock fed without addition of glycosylamides of the formula (I).

EXAMPLES

Thin-layer chromatography (TLC) was carried out on ready-coated silica gel TLC plates (E. Merck, Darmstadt) and the preparative separations were carried out on silica gel 60 (Merck, Darmstadt).

Mobile phase systems: System G $CH_2Cl_2/CH_3OH/15\%$ strength ammonium hydroxide in the ratio 1/1/1, taking the lower phase; system E $CH_2Cl_2/CH_3OH$ 20% strength ammonium hydroxide in the ratio 8/4/1; parts by volume in each case.

EXAMPLE 1

N-D-Glucopyranosyloleamide 3 g of 2,3,4,6-tetra-O-acetyl-3,D-glucopyranosylamine were dissolved in 25 ml of tetrahydrofuran and, after addition of 3.45 g of sodium carbonate, 2.24 g of oleoyl chloride dissolved and in 5 ml of tetrahydrofuran (THF) were added dropwise, with vigorous stirring and cooling at 0° C. After reaction was complete (checked by thin-layer chromatography=TLC in the system toluene: acetone=4:1), the precipitate was filtered off, and the filtrate was evaporated in vacuo and dried. For the O-deacetylation, the crude product thus obtained was dissolved in 200 ml of a solution of methanol/triethylamine water=4:3:1 (parts by volume) and left a room temperature for 15 hours. The solution was then evaporated in vacuo and the residue was chromatographed on silica gel. The title product obtained in this manner had a Rf value of 0.46.

EXAMPLE 2

N-Benzyl-β-D-glucopyranosylamine 50 g of D-glucose are dissolved in 1,000 ml of hot ethanol and, after addition of 89 g of benzylamine, left at room temperature for 48 hours. The mixture is then cooled in ice and the product is precipitated with petroleum ether. It is filtered off with suction, washed with ether and dried in vacuo.

$^1$H-NMR in $CD_3OD$: δ=7.33 broad singlet phenyl-H.

EXAMPLE 3

N-Benzyl-N-glucopyranosylacetamide 1 g of the compound from Example 2 in 10 ml of absolute pyridine at 0° C. is acetylated with 6 ml of acetic anhydride at room temperature. The mixture is worked up as usual and 1 g of N-acetyl-tetra-O-acetyl derivative is obtained.

$^1$H-NMR in $CD Cl_3$: δ=1.9−2.1 m 5×$CH_3$—CO—.

For the O-deacetylation, 500 ml of the pentaacetate in absolute methanol are deacetylated with 10% sodium methylate and worked up as usual. The product results as an amorphous solid.

$^1$H-NMR in $CD_3OD$: δ=7.1-7.4 phenyl-H.

EXAMPLE 4

N-Dodecyl-β-D-glucopyranosylamine 18 g of glucose are stirred in 50 ml of ethanol at 70° C., then 18.5 g of dodecylamine are added, heating is continued until a clear solution is obtained, and this is allowed to cool to room temperature and, after 20 hours, the crystals which have separated out are filtered off with suction. They are washed with ethanol and ether and dried in vacuo.

Yield=24 g.

Elemental analysis: ($C_{18}H_{37}NO_5$=347): calculated: C=62.2%, H=10.6%, N=4.0%, found: C=62.2%, H=10.6%, N=4.2%.

EXAMPLE 5

N-Dodecyl-N-β-D-glucopyranosylacetamide

Preparation is carried out in analogy to Example 3.

Elemental analysis: calculated: C=61.7%, H=10.0%, N=3.6%, found: C=60.8%, H=9.9%, N=3.8%.

EXAMPLE 6

N-Glucopyranosyl-N-propyloleamide 11 g of N-propyl-D-glucopyranosylamine in 90 ml of tetrahydrofuran (THF) are stirred with 21 g of sodium carbonate, then 1 equivalent of oleoyl chloride in 20 ml of THF is slowly added dropwise to this, with cooling. After N-acylation is complete (checked by TLC in the mobile phase system $CH_2Cl_2/CH_3OH$=13:1), the precipitate is filtered off with suction, washed with THF, and the filtrates are evaporated in vacuo and the resulting syrup is chromatographed on silica gel for subsequent purification. Development of the column with $CH_2Cl_2$ $CH_3OH$=15:1.

The fractions which contain the pure title compound are combined. The solvent is removed in vacuo.

Yield: 3.3 g.

Rf value: 0.34 in $CH_2Cl_2/CH_3OH$=15:1.

$[\alpha]_D^{20}$= +7.5° (c=1.0 $CH_2Cl_2$)

EXAMPLE 7

N-Glucopyranosyl-N-hexyloleamide

Preparation is carried out as described in Example 6, starting from N-hexyl-D-glucopyranosylamine. Column chromatography with $CH_2Cl_2/CH_3OH$=13:1.

Yield: 9.2 g of pure product.

Rf value=0.38 in $CH_2Cl_2/CH_3OH$=13:1.

$[\alpha]_D^{20}$= +5.8° C. (c=0.94 in $CH_2Cl_2$).

EXAMPLE 8

N-Glucopyranosyl-N-(n-3,3,3-trifluoropropyl)oleamide 3.6 g of glucose and 0.8 ml of 0.5N hydrochloric acid and 4.6 g of n-3,3,3-trifluoropropylamine are heated, with stirring, at 75° C. for 25 minutes. After cooling, the N-glucoside crystallizes out, and is washed with ether and dried in vacuo.

Yield: 4.1 g.

The N-acylation with oleoyl chloride is carried out in analogy to Example 6. Column chromatography with $CH_2Cl_2/CH_3OH$=15:1.

Yield: 2.7 g.

$[\alpha]_D^{20}$= +7.6° (c=1.0 in $CH_2Cl_2$).

EXAMPLE 9

N-(2-Ethylhexyl)-N-glucopyranosyloleamide

The reaction of glucose with 2-ethylhexylamine is carried out in analogy to Example 8. The N-acylation with oleoyl chloride is carried out in analogy to Example 6. Column chromatography with $CH_2Cl_2/CH_3OH$=15:1.

Rf value of the title compound: 0.44 in $CH_2/Cl_2/CH_3OH$=15/1.

EXAMPLE 10

N-(3-Butoxypropyl)-N-glucopyranosyloleamide

Preparation of the N-glycoside and N-acylation as described in Example 8 and Example 6 respectively.

Rf value: 0.29 mobile phase system $CH_2Cl_2/CH_3OH$=10/1.

EXAMPLE 11

N-Dodecyl-N-glucopyranosylstearamide 100 g of N-dodecyl-β-D-glucopyranosylamine from Example 4 are dissolved in 765 ml of THF and, in the presence of 32 g of triethylamine, 80 g of stearoyl chloride are added dropwise, with cooling.

To work up, the mixture is filtered and the solvent is removed in vacuo.

N-Dodecyl-N-glucopyranosyloleamide is prepared in the same manner.

EXAMPLE 12

N-Decyl-N-glucopyranosyloleamide 18 g of D-glucose and 50 ml of ethanol are stirred with 15.7 g of decylamine at 70° C. until a clear solution is produced. This is then allowed to cool to room temperature and, after 4 hours, the crystals are filtered off with suction and washed with ethanol and ether. Yield: 20 g.

The latter are stirred with 22.6 g of sodium carbonate in 166 ml of THF. Then, at 25° C., 19 g of oleoyl chloride in 20 ml of THF are slowly added dropwise. After a further hour, the mixture is filtered with suction, the filtrate is evaporated to a syrup in vacuo, and the crude product is purified by column chromatography on silica gel using the eluting agent $CH_2Cl_2/CH_3OH=13/1$.

Rf value of the title compound=0.53 in $CH_2Cl_2/CH_3OH=13/2$.

EXAMPLE 13

N-Glucopyranosyl-N-tetradecyloleamide

Preparation in analogy to Example 12.

Column chromatography with the eluting agent $CH_2Cl/_2CH_3OH=13/1$.

$[\alpha]_D^{20}=+9.6$ (c=1.0 DMF).

Elemental analysis: calculated: C=70.3%, H=11.3%, N=2.16%, found: C=69.4%, H=11.6%, N=2.1%.

EXAMPLE 14

N-Glucopyranosyl-N-hexadecyloleamide

Preparation and purification in analogy to Example 12.

Rf value 0.25 mobile phase $CH_2Cl_2/CH_3OH=13/1$.

EXAMPLE 15

N-Glucopyranosyl-N-octadecyloleamide 90 g of D-glucose and 135 g of octadecylamine in 1,000 ml of 2-propanol and 500 ml of water are heated at 50° C., with stirring, until a clear solution results. This is then left at room temperature overnight. The product is now filtered off with suction, washed with alcohol and ether, dried and finally recrystallized from ethanol THF. 10 g of this N-octadecyl-β-D-glucopyranosylamine are suspended in 80 ml of THF and, after addition of 10 g of sodium carbonate, 7 g of oleoyl chloride in 10 ml of THF are added dropwise. After reaction is quantitative (TLC in $CH_2Cl_2/CH_3OH=13/1$), working up is carried out as described in Example 12. Column purification and eluting agent $CH_2Cl_2/CH_3OH=13/1$.

RF value=0.35 mobile phase system $CH_2Cl_2/CH_3OH=9/1$.

EXAMPLE 16

N-Glucopyranosyl-N-octadecylstearamide

Preparation in analogy to Example 6 from N-octadecylglucopyranosylamine and stearoyl chloride.

Elemental analysis: calculated: C=72.5%, H=11.7%, N=2.0%, found: C=71.7%, H=12.2%, N=2.0%.

EXAMPLE 17

N-Glucosyl-N-octadecyldodecanoamide

Preparation in analogy to Example 16 from N-octadecyl-β-D-glucopyranosylamine and dodecanoyl chloride.

$[\alpha]_D^{20}=+8°$ (C=1.0 dioxane).

EXAMPLE 18

N-Glucosyl-N-octadecyltetradecanoamide

Preparation in analogy to Example 16 from N-octadecyl-β-D-glucopyranosylamine and tetradecanoyl chloride $[\alpha]_D^{20}=+9.5°$ (C=1.0 DMF).

Elemental analysis: calculated: C=71.8%, H=11.7%, N=2.1%, found: C=71.3%, H=11.9%, N=1.9%.

EXAMPLE 19

N-(2-Acetamido-2-deoxy-D-glucopyranosyl)-N-dodecyloleamide 15 g of N-acetyl-D-glucosamine and 18.8 g of dodecylamine in 50 ml of ethanol are heated, with stirring, at 80° C. for 3 hours. Then insolubles are filtered off while hot, the filtrate is cooled, and the precipitated product is filtered off with suction and washed with ethanol and ether 2.2 g of the 2-acetamido-2-deoxy-N-octadecylglucopyranosylamine thus obtained are stirred with 2 g of sodium carbonate in 17 ml of THF. Then 1.45 g of oleoyl chloride in 5 ml of THF are added dropwise.

Working up is carried out as described in Example 6.

Column chromatography with the eluting agent $CH_2Cl_2/CH_3OH=20/1$.

$[\alpha]_D^{20}=+9.2°$ (c=0.56 $CH_3OH$).

Elemental analysis: calculated: C=72.8%, H=11.7%, N=3.8%, found: C=72.9%, H=12.5%, N=3.3%.

EXAMPLE 20

N-Octadecyl-L-rhamnopyranosylamine 9 g of L-rhamnose and 13.5 g of stearylamine in 100 ml of 2-propanol and 50 ml of water are stirred at 50° C. until a clear solution has resulted. After 50 hours at room temperature, the crystals are filtered off with suction, washed with ethanol and ether and dried in vacuo.

Yield: 17.4 g-.

EXAMPLE 21

N-Octadecyl-N-rhamnopyranosyloleamide 7 g of the compound from Example 20 are acylated with oleoyl chloride as described in Example 6. Column separation in $CH_2Cl_2/CH_3OH=13/1$.

Elemental analysis: calculated: C=74.4%, H=11.9%, N=2.04%, found: C=74.3%, H=12.0%, N=2.1%.

EXAMPLE 22

N-Octadecyl-L-fucopyranosylamine 3.26 g of L-fucose and 5.38 g of stearylamine in 20 ml of ethanol are heated at 70° C., with stirring, until a clear solution has resulted. This is allowed to cool and, when crystallization is complete, the solid is filtered off with suction and washed with ethanol and ether.

Yield after drying in vacuo: 4.4 g.

EXAMPLE 23

N-Fucopyranosyl-N-octadecyloleamide 2.9 g of the compound from Example 22 are acylated with oleoyl chloride as described in Example 6. Column chromatography with the eluting agent $CH_2Cl_2/CH_3OH=15/1$.

Yield of pure product: 1.9 g.

RF value=0.44 mobile phase system as for column chromatography.

EXAMPLE 24

N-(β-D-Arabinopyranosyl)-N-octadecyloleamide 7 g of N-octadecyl-β,D-arabinopyranosylamine are acylated with oleoyl chloride as described in Example 6. Column chromatography with eluting agent $CH_2Cl_2/CH_3OH=20/1$.

Yield of pure product: 2.3 g.

RF value=0.57 mobile phase $CH_2Cl_2/CH_3OH=15/1$.

$[\alpha]_D^{20}=+20°$ (c=1.03 $CH_2CC_2$).

EXAMPLE 25

N-(β,D-Maltosyl)-N-octadecyloleamide 3.04 g of N-octadecyl-β-D-maltosylamine are acylated with oleoyl chloride as described in Example 6.

Column chromatography in $CH_2Cl_2/CH_3OH=10/1$.

RF value: 0.24 mobile phase $CH_2Cl_2/CH_3OH=8,1$.

$[\alpha]_D^{20}=+22°$ C. (c=0.5 $CH_3OH$).

EXAMPLE 26

N-(4-Azido-4-deoxy-D-glucopyranosyl)-N-octadecyl-dodecanoamide 3.09 g of 4-azido-4-deoxy-D-glucose are dissolved in 30 ml of isopropanol and 15 ml of water and, after addition of 4.05 g of octadecylamine, the solution is heated to 50° C.

The resulting solution is allowed to stand at room temperature overnight. The resulting solid is filtered off, washed with a little ethanol and ether and dried.

2.3 g of this product are dissolved in 10 ml of THF, and 3 g of sodium carbonate and 1.2 g of dodecanoyl chloride, dissolved in 15 ml of THF, are added. After reaction is quantitative, the mixture is worked up as described in Example 12.

Rf value: 0.27 in $CH_2Cl_2/CH_3OH=4:1$ (V/V).

EXAMPLE 27

N-(4-Acetamido-4-deoxy)-D-glucopyranosyl-N-octadecyloleamide 3 g of the compound from Example 26 in 30 ml of dioxane/methanol=2/1 and 3 ml of acetic anhydride are hydrogenated under atmospheric pressure in the presence of 1.0 g of palladium/charcoal (5%). When reaction is complete (mobile phase system $CH_2Cl_2/CH_3OH=3/1$), the catalyst is filtered off and the filtrate is evaporated in vacuo.

Rf value: 0.18 ($CH_2Cl_2$/MeOH, 10:1 V/V).

EXAMPLE 28

N-(6-Deoxy-6-fluoro-D-glucopyranosyl)-N-octadecyloleamide 18.2 g of 6-deoxy-6-fluoro-D-glucose and 13.5 g of octadecylamine and 7 g of oleoyl chloride are reacted and worked up as described in Example 15.

Rf value: 0.30 in $CH_2Cl_2/CH_3OH=9/1$.

EXAMPLE 29

N-(Methyl-D-glucopyranosyluronato)-N-octadecyloleamide 15 g of D-glucuronolactone are dissolved in 150 ml of absolute methanol and allowed to stand at room temperature with 3 ml of 1N sodium methanolate solution for half an hour. The mixture is then neutralized with acid ion exchanger, and is evaporated. The resulting methyl glucuronate is reacted and worked up as described in Example 15 to give the title compound.

Rf value: 0.32 ($CH_2Cl_2/CH_3OH=9:1$, V/V).

EXAMPLE 30

N-(Glucuronopyranosyl)-N-octadecyloleamide 2 g of the compound described in Example 29 are dissolved in 10 ml of dioxane and, after addition of 5 ml of 1N sodium hydroxide solution, the mixture is heated to reflux for 2 h. After cooling, the mixture is neutralized with dilute hydrochloric acid, evaporated in vacuo, and the residue is stirred with 20 ml of methanol/dioxane=1/1. It is then filtered and the filtrate is evaporated to a syrup.

Rf value: 0.13 ($CH_2Cl_2/CH_3OH=7:1$, V/V).

EXAMPLE 31

N-(4-Amino-4-deoxy-D-glucopyranosyl)-N-octadecyl-lauramide 3 g of the compound from Example 26 in 30 ml of dioxane/methanol 2/1 are hydrogenated in the presence of 1.0 g of palladium/charcoal (5%). After reaction is complete, the catalyst is filtered off and the filtrate is evaporated in vacuo.

Rf value: 0.39 $CH_2Cl_2$/MeOH 5:1.

EXAMPLE 32

N-(4-Lauramido-4-deoxy-D-glucopyranosyl)-N-octadecyllauramide 2.0 g of sodium carbonate are added to 4.00 g of the compound described in Example 31 in 30 ml of THF and it is reacted with 1.42 g of dodecanoyl chloride in 10 ml of THF. After 30 minutes, the mixture is diluted with dichloromethane, then filtered and the filtrate is evaporated in vacuo. The syrup is purified by column chromatography (mobile phase dichloromethane/methanol=15:1).

Rf value: 0.36 $CH_2Cl_2$/MeOH 10:1.

EXAMPLE 33

N-Glucopyranosyl-N-octadecylpalmitamide

Preparation in analogy to Example 16 from N-octadecylglucopyranosylamine and palmitoyl chloride.

Rf value: 0.36 $CH_2Cl_2$/MeOH 9:1.

EXAMPLE 34

N-Octadecyl-N-glucopyranosyllauramide

Preparation in analogy to Example 16 from N-octadecylglucopyranosylamine and lauroyl chloride.

Rf value: 0.35 $CH_2Cl_2/CH_3OH$ 9:1.

EXAMPLE 35

N-Octadecyl-N-rhamnopyranosylstearamide

Preparation in analogy to Example 21 from N-octadecylrhamnopyranosylamine and stearoyl chloride.

Rf value: 0.39 $CH_2Cl_2/CH_3OH$ 9:1.

EXAMPLE 36

N-Octadecyl(2-amino-2-deoxy-D-glucopyranosyl)amine hydrochloride 6.45 g of D-glucosamine hydrochloride are dissolved in 30 ml of isopropanol and 10 ml of water at 60° C., and 12.1 g of stearylamine are added. The resulting clear solution is stirred for a further 10 min and then cooled to room temperature. The product which has crystallized out is filtered off with suction and washed first with ethanol/water (5:2, v/v), then with ethanol and finally with ether. The residue is dried under high vacuum.

EXAMPLE 37

N-Octadecyl-N-(2-dodecylamido-2-deoxy-D-glucopyranosyl)dodecanoamide 4.6 g of the compound described in Example 36 are suspended in 120 ml of tetrahydrofuran, and 22.6 g of sodium carbonate are added. 4.2 g of dodecanoyl chloride in 20 ml of tetrahydrofuran are added dropwise to the stirred suspension. The mixture is evaporated in vacuo, acetylated with 50 ml of pyridine and 25 ml of acetic anhydride, then poured onto ice-water, taken up in dichloromethane, and the organic phase is washed consecutively with dilute hydrochloric acid, saturated sodium bicarbonate solution and then with water, dried over sodium sulphate and evaporated to a syrup in vacuo. The resulting syrup is purified by column chromatography (mobile phase toluene/ethyl acetate=10:1, v/v). The resulting solid (melting point 86°) is dissolved in absolute methanol, 20 mg of sodium methoxide are added, and the mixture is heated under reflux for 20 minutes. After reaction is complete, the mixture is neutralized with acid ion exchanger, and evaporated in vacuo.

Melting point: 78° C., Rf value: 0.64 in $CH_2Cl_2/MeOH=10/1$ (v/v).

EXAMPLE 38

N-Propyl(2-amino-2-deoxy-D-glucopyranosyl)amine hydrochloride 21.5 g of glucosamine hydrochloride are suspended in 17.7 g of n-propylamine and heated at 70° C. until a clear solution is produced. On cooling to room temperature, the product precipitated out.

EXAMPLE 39

N-Propyl-N-(2-oleamido-2-deoxy-D-glucopyranosyl)oleamide 5.1 g of the compound described in Example 38 are suspended in 100 ml of tetrahydrofuran, and 12.7 g of sodium carbonate are added. Then 12 g of oleoyl chloride in 20 ml of tetrahydrofuran are added dropwise. After reaction is complete, the mixture is diluted with 50 ml of dichloromethane, and the sodium salt is filtered off and washed with water, and the filtrate is dried over sodium sulphate and evaporated in vacuo. The resulting syrup is purified by column chromatography (mobile phase dichloromethane/methanol 15/1, v/v).

Rf value: 0.37 in $CH_2Cl_2/MeOH$ 10:1.
$\alpha_D = 17.9°$ (c=1.02 in dichloromethane).

EXAMPLE 40

N-Glucopyranosyl-N-tetradecylstearamide

Preparation in analogy to Example 11 from N-tetradecylglucopyranosylamine and stearoyl chloride.
Rf value: 0.25 in toluene/acetone 1:1.

EXAMPLE 41

N-Dodecyl-N-(2-amino-2-deoxyglucopyranosyl)amine hydrochloride 46 g of dodecylamine are fused at 60°, and 31 g of glucosamine hydrochloride are added with stirring. After cooling to room temperature, the product precipitates out. The solid is stirred with ether three times, filtered off with suction and then dried under high vacuum.

EXAMPLE 42

N-Dodecyl-N-(2-stearylamido-2-deoxy-D-glucopyranosyl)stearamide 5 g of the compound described in Example 41 are suspended in 100 ml of tetrahydrofuran, and 8.5 g of sodium carbonate and 8 g of stearoyl chloride in 20 ml of tetrahydrofuran are added. After reaction is complete, the mixture is worked up as described in Example 39. The resulting crude syrup is crystallized from ethyl acetate.

Melting point 67°.
Rf value 0.42 in $CH_2Cl_2/MeOH$ 10/1.

EXAMPLE 43

N-Dodecyl-N-(2-lauramido-2-deoxy-D-glucopyranosyl)lauramide 5 g of the compound described in Example 41 are reacted with lauroyl chloride as described in Example 42.

Melting point 67°.
Rf value 0.42 in $CH_2Cl_2/MeOH$ 10/1.

EXAMPLE 44

N-Octadecyl-N-(galactopyranosyl)amine 60 g of D-galactose are suspended in 330 ml of isopropanol and 170 ml of water, and the mixture is heated to 50°. After addition of 90 g of stearylamine, the mixture is stirred until all the amine has gone into solution. On cooling, the glycosylamine crystallizes out. The solid is filtered off with suction, washed consecutively with ethanol and with ether, and dried in vacuo.

EXAMPLE 45

N-Octadecyl-N-(D-galactopyranosyl)lauramide

Preparation from 8.4 g of the compound described in Example 44 and 4.4 g of dodecanoyl chloride in analogy to Example 11.

Rf value: 0.22 in toluene-n-propanol 4/1 (v/v).
$\alpha_D = 11.4°$ (c=0.93 in dichloromethane).

EXAMPLE 46

N-Tetradecyl-N-(D-galactopyranosyl)oleamide

N-Tetradecyl-N-(D-galactopyranosyl)amine is prepared from 30 g of D-galactose and 53 g of tetradecylamine as described in Example 44. The galactoxylamine is reacted with oleoyl chloride by the process described in Example 11.

Rf value: 0.26 in toluene/n-propanol 4/1 (v/v).
$\alpha = 11°$ (c=1.0 in dichloromethane).

EXAMPLE 47

N-Octadecyl-N-mannopyranosylamine 20 g of D-mannose and 45 g of stearylamine are reacted to give the glycosylamine as described in Example 44.

EXAMPLE 48

N-Octadecyl-N-(D-mannopyranosyl)lauramide 8.6 g of the compound described in Example 47 are reacted with 4.4 g of dodecanoyl chloride as described in Example 11.

Rf value: 0.25 in toluene/n-propanol 4/1 (v/v).

19

$\alpha_D = 11.3°$ (c=1.13 in dichloromethane).

EXAMPLE 49

N-Octadecyl-N-(D-mannopyranosyl)tetradecanoamide

Preparation from the compound described under Example 47 and tetradecanoyl chloride in analogy to Example 11.

Rf value: 0.26 in toluene/n-propanol 4/1 (v/v).
$\alpha = 9.9°$ (c=1.0 in dichloromethane).

EXAMPLE 50

N-Tetradecyl-N-(D-mannopyranosyl)oleamide 20 g of D-mannose and 35 g of tetradecylamine are reacted to give the N-tetradecylmannopyranosylamine as described in Example 44. In a second reaction step, the glycosylamine (7.5 g) is reacted with 6.0 g of oleoyl chloride to give the glycosylamide as described in Example 11.

Rf value: 0.29 in toluene/n-propanol 4/1 (v/v).
$\alpha = 10.8°$ (c=1 in tetrahydrofuran).

EXAMPLE 51

2-Dodecylamido-2-deoxy-D-glucopyranose 55 g of dodecanoyl chloride are dissolved in 170 ml of tetrahydrofuran and, with vigorous stirring, added dropwise to a solution of 54 g of D-glucosamine hydrochloride in 330 ml of aqueous sodium carbonate solution (20%). After completion of the addition of the acid chloride, the mixture is stirred for a further hour, and then 500 ml of water is added and the solid is filtered off with suction and washed with water. The residue is recrystallized from isopropanol/water 10/1 (v/v) and dried under high vacuum.

EXAMPLE 52

N-Dodecyl-N-(2-dodecylamido-2-deoxy-D-glucopyranosyl)amine 45 g of dodecylamine and 75 ml of ethanol are added to 15 g of the compound described in Example 51, and the mixture is heated to 70° with stirring. After a clear solution has formed, it is cooled to room temperature and crystallization allowed to take place overnight. The precipitated solid is filtered off with suction, washed once with ethanol and three times with ether and dried in vacuo.

EXAMPLE 53

N-Dodecyl-N-(2-dodecylamido-2-deoxy-D-glucopyranosyl)stearamide 4 g of the compound described in Example 52 are dissolved in 100 ml of tetrahydrofuran, and 4.8 g of sodium carbonate are added. 3.45 g of stearoyl chloride dissolved in 20 ml of tetrahydrofuran are added dropwise to this suspension, with stirring. Stirring is continued for 30 minutes, then the mixture is diluted with 50 ml of dichloromethane and the solid is filtered off with suction. The residue is washed with dichloromethane. The organic solvent phases are combined and evaporated in vacuo. The resulting syrup is purified by chromatography (mobile phase: dichloromethane/methanol 20/1 (v/v)).

Rf value: 0.55 in dichloromethane/methanol 10/1 (v/v).
$\alpha = 15.8°$ (c=1.05 in dichloromethane).

EXAMPLE 54

N-Dodecyl-N-(2-acetamido-2-deoxy-D-glucopyranosyl)tetradecanoamide 26 g of N-acetylglucosamine are dissolved in 100 ml of ethanol and 60 ml of water and the solution is heated to 60°. 37 g of dodecylamine are added and the mixture is stirred until a clear solution appears. After cooling to room temperature, the glycosylamine crystallizes out. The mass of crystals is filtered off with suction, washed with ethanol and then with ether and dried in vacuo. 3 g of the solid are suspended in 50 ml of tetrahydrofuran, 3.3 g of sodium carbonate are added and 1.9 g of tetradecanoyl chloride in 10 ml of tetrahydrofuran are added. After reaction is complete, the mixture is diluted with 30 ml of dichloromethane, filtered and the filtrate is evaporated in vacuo. The resulting syrup is purified by chromatography (mobile phase dichloromethane/methanol 20/1, (v/v)).

Rf value: 0.21 in dichloromethane/methanol 10/1 (v/v).

EXAMPLE 55

N-Dodecyl-N-(2-acetamido-2-deoxy-D-glucopyranosyl)stearamide 3 g of N-(2-acetamido-2-deoxy)dodecylamine, the preparation of which is described in Example 54, are reacted with stearoyl chloride as described in Example 54.

Rf value: 0.23 in dichloromethane/methanol 10/1 (v/v).

EXAMPLE 56

N-Octadecyl-N-(2-acetamido-2-deoxy-D-glucopyranosyl)tetradecanoamide

Preparation in analogy to Example 19 from N-acetylglucosamine, stearylamine and tetradecanoyl chloride.

Rf value: 0.25 in toluene/isopropanol 4/1 (v/v).
$\alpha = 16.9°$ (c=1 in tetrahydrofuran).

EXAMPLE 57

N-Dodecyl-N-(D-mannopyranosyl)stearamide

Preparation from D-mannose, dodecylamine and stearoyl chloride in analogy to Example 11.

Rf value: 0.28 in toluene/n-propanol 4/1 (v/v).
$\alpha = 11.4°$ (c=1 in tetrahydrofuran).

EXAMPLE 58

N-Dodecyl-N-(d-galactopyranosyl)stearamide

Preparation from D-galactose, dodecylamine and stearoyl chloride in analogy to Exaple 11.

Rf value: 0.28 in toluene/n-propanol 4/1 (v/v).
$\alpha = 4.4°$ (c=1 in dichloromethane).

EXAMPLE 59

N-Dodecyl-N-(2-acetamido-2-deoxy-D-glucopyranosyl)dodecanoamide

Preparation in analogy to Example 54 from N-acetylglucosamine, dodecylamine and dodecanoyl chloride.

Rf value: 0.21 in dichloromethane/methanol 10/1 (v/v)

EXAMPLE 60

N-Dodecyl-N-(D-ribopyranosyl)dodecanoamide 10 g of D-ribose are dissolved in 180 ml of isopropyl alcohol/water 2/1 (v/v) and the solution is heated to 70° C. 18 g of dodecylamine are added. After a clear solution has formed, the temperature is maintained for a further 15 minutes. The mixture is cooled to room temperature and evaporated in vacuo. 10 g of the resulting syrup are dissolved in 100 ml of tetrahydrofuran and 10 ml of methanol. After addition of 10 g of sodium carbonate, the mixture is cooled to 0° C. 5.5 g of dodecanoyl chloride, dissolved in 20 ml of tetrahydrofuran, are added dropwise. After reaction is complete, the mixture is worked up as usual and the product is purified by column chromatography.

$\alpha_D = 5.3°$ (c=1.1 in tetrahydrofuran).

It will be understood that the specification and examples are illustrative but not limitative of the present invention and that other embodiments within the spirit and scope of the invention will suggest themselves to those skilled in the art.

We claim:

1. A method of promoting the growth of animals which comprises administering to such animals a growth promoting effective amount of a compound of the formula

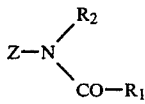

in which

Z is a glycosyl radical bonded via the anomeric carbon atom, $R_1$ is hydrogen or an optionally substituted hydrocarbon radical having up to 30 Carbon atoms optionally interrupted by O, N or S, and $R_2$ is hydrogen or an alkyl or aralkyl radical having up to 30 Carbon atoms optionally interrupted by O or substituted by groups containing oxygen or by halogen, with the proviso that $COR_1$ is not an acyl group having 1–5 Carbon atoms when $R_2$ is an alkyl group having 10–20 Carbon atoms.

2. A method according to claim 1, in which $R_1$ is an alkyl or alkenyl radical having 1–20 carbon atoms.

3. A method according to claim 1, in which $R_2$ is an alkyl or alkenyl radical having 1–20 Carbon atoms.

4. A method according to claim 1, in which X is a monosaccharide radical which is optionally substituted by an acylamido group.

5. The method according to claim 1, wherein the compound is N-octadecyl-N-D-glucopyranosyllauramide, N-dodecyl-N-D-galactopyranosyl stearamide, N-octadecyl-N-D-glucopyranosyloleamide or N-dodecyl-N-(2-acetamido-2-deoxy-D-glucopyranosyl)-dodecanoamide.

6. The method according to claim 1, wherein the compound is added to the animals' food.

* * * * *